(12) United States Patent
Ganem

(10) Patent No.: US 9,737,410 B2
(45) Date of Patent: Aug. 22, 2017

(54) INTERVERTEBRAL PROSTHESIS FOR INTRODUCTION VIA POSTERIOR APPROACH

(71) Applicant: ORTHOPAEDIC & SPINE DEVELOPMENT (OSD), Avignon (FR)

(72) Inventor: Franck Ganem, Caen (FR)

(73) Assignee: ORTHOPAEDIC & SPINE DEVELOPMENT (OSD), Avignon (FR)

( * ) Notice: Subject to any disclaimer, the term of this patent is extended or adjusted under 35 U.S.C. 154(b) by 0 days.

(21) Appl. No.: 14/894,871

(22) PCT Filed: May 30, 2014

(86) PCT No.: PCT/FR2014/051287
§ 371 (c)(1),
(2) Date: Nov. 30, 2015

(87) PCT Pub. No.: WO2014/191701
PCT Pub. Date: Dec. 4, 2014

(65) Prior Publication Data
US 2016/0113773 A1   Apr. 28, 2016

(30) Foreign Application Priority Data

May 31, 2013   (FR) ..................... 13 01257

(51) Int. Cl.
*A61F 2/44*  (2006.01)
*A61F 2/30*  (2006.01)
*A61F 2/28*  (2006.01)

(52) U.S. Cl.
CPC .......... *A61F 2/442* (2013.01); *A61F 2/30965* (2013.01); *A61F 2/446* (2013.01);
(Continued)

(58) Field of Classification Search
CPC .... A61F 2/30965; A61F 2/442; A61F 2/4455; A61F 2002/4475
See application file for complete search history.

(56) References Cited

U.S. PATENT DOCUMENTS 7,527,629 B2 * 5/2009 Link ................. A61B 17/1757
606/87
8,187,334 B2 * 5/2012 Curran .................... A61F 2/447
623/17.16
(Continued)

FOREIGN PATENT DOCUMENTS

FR        2946245 A1   12/2010

OTHER PUBLICATIONS

Jun. 22, 2015 International Search Report issued in International Patent Application No. PCT/FR2014/051287.

*Primary Examiner* — Ellen C Hammond
*Assistant Examiner* — Stuart S Bray
(74) *Attorney, Agent, or Firm* — Oliff PLC

(57) ABSTRACT

An intervertebral prosthesis for insertion by posterior approach, designed to be inserted in pairs between two vertebral bodies, said prosthesis consisting of a prosthesis body extending in a longitudinal direction of intervertebral insertion, including peripheral faces delimiting, on the inside, an inner space for receiving a bone substitute. The prosthesis includes a prosthesis body of which the lower and upper bearing faces have a convex profile having continuously variable convexity in the longitudinal direction. The invention is intended for the treatment of individuals suffering from disc degeneration in the thoracic or lumbar vertebrae.

11 Claims, 7 Drawing Sheets

(52) U.S. Cl.
CPC ...... *A61F 2/447* (2013.01); *A61F 2002/2835* (2013.01); *A61F 2002/3008* (2013.01); *A61F 2002/30281* (2013.01); *A61F 2002/30779* (2013.01); *A61F 2002/30784* (2013.01); *A61F 2002/30828* (2013.01); *A61F 2002/30904* (2013.01); *A61F 2002/30971* (2013.01); *A61F 2002/4475* (2013.01); *A61F 2310/00017* (2013.01); *A61F 2310/00023* (2013.01)

(56) References Cited

U.S. PATENT DOCUMENTS

| | | | | |
|---|---|---|---|---|
| 2004/0127990 A1* | 7/2004 | Bartish, Jr. | ............ | A61F 2/4611 623/17.11 |
| 2004/0199251 A1* | 10/2004 | McCombe | ............ | A61F 2/4455 623/17.11 |
| 2008/0221694 A1* | 9/2008 | Warnick | ............ | A61F 2/4465 623/17.16 |
| 2008/0275506 A1* | 11/2008 | Baynham | ............ | A61F 2/447 606/261 |
| 2009/0182341 A1* | 7/2009 | Link | ............ | A61B 17/1757 606/99 |
| 2009/0276049 A1* | 11/2009 | Weiland | ............ | A61F 2/4465 623/17.16 |
| 2010/0094422 A1* | 4/2010 | Hansell | ............ | A61F 2/4611 623/17.16 |
| 2011/0230965 A1* | 9/2011 | Schell | ............ | A61F 2/447 623/17.11 |
| 2011/0276142 A1* | 11/2011 | Niemiec | ............ | A61F 2/442 623/17.16 |
| 2012/0083884 A1* | 4/2012 | Milz | ............ | A61F 2/4465 623/17.16 |
| 2012/0083887 A1* | 4/2012 | Purcell | ............ | A61F 2/447 623/17.16 |
| 2012/0209383 A1* | 8/2012 | Tsuang | ............ | A61F 2/4603 623/17.12 |
| 2013/0110241 A1* | 5/2013 | Palmatier | ............ | A61F 2/4611 623/17.16 |
| 2013/0274884 A1* | 10/2013 | Matsumoto | ............ | A61F 2/44 623/17.16 |
| 2014/0039626 A1* | 2/2014 | Mitchell | ............ | A61F 2/447 623/17.16 |
| 2014/0058512 A1* | 2/2014 | Petersheim | ............ | A61F 2/4465 623/17.16 |
| 2014/0094919 A1* | 4/2014 | Mantri | ............ | A61F 2/442 623/17.16 |
| 2014/0172105 A1* | 6/2014 | Frasier | ............ | A61F 2/4611 623/17.16 |
| 2014/0257486 A1* | 9/2014 | Alheidt | ............ | A61F 2/447 623/17.15 |
| 2014/0277505 A1* | 9/2014 | Mitchell | ............ | A61L 27/10 623/17.16 |
| 2015/0100129 A1* | 4/2015 | Waugh | ............ | A61F 2/4455 623/17.16 |
| 2016/0106551 A1* | 4/2016 | Grimberg, Jr. | ............ | A61F 2/4601 623/17.16 |
| 2016/0193055 A1* | 7/2016 | Ries | ............ | A61F 2/442 623/17.16 |
| 2016/0199193 A1* | 7/2016 | Willis | ............ | A61F 2/44 623/17.16 |
| 2016/0270930 A1* | 9/2016 | Siegal | ............ | A61F 2/447 |
| 2016/0296343 A1* | 10/2016 | Bost | ............ | A61F 2/4455 |
| 2016/0324653 A1* | 11/2016 | Flickinger | ............ | A61F 2/2846 |

\* cited by examiner

INTERVERTEBRAL PROSTHESIS FOR INTRODUCTION VIA POSTERIOR APPROACH

The present invention concerns an intersomatic prosthesis for introduction via posterior approach, in other words a prosthesis for spacing vertebral bodies.

It concerns more particularly an intersomatic prosthesis designed to be introduced in pairs between two vertebral bodies, and more particularly between the vertebral bodies of overlying and underlying thoracic or lumbar vertebrae of a vertebral column, and the geometry of which allows an individualized setting of the lordosis angle that the surgeon wants to give to the vertebral segment.

The invention thus concerns the technical field of intersomatic prostheses, also called intersomatic cages, used in orthopedic surgery operations of the vertebral column, particularly in the treatment of individuals suffering from degenerative disc disease at the thoracic or lumbar vertebrae.

The prosthesis according to the invention is intended to be implanted via posterior approach between two adjacent vertebral bodies instead of a defective disc, and more specifically to be implanted in duplicate, in order to ensure fusion between the vertebral bodies and thus allow reestablish the intradiscal height and especially restore an individualized physiological lordosis depending on the patient.

It is known to use intersomatic prostheses to reestablish the space called intradiscal space between two adjacent vertebrae, by interposing at least one prosthesis within this intradiscal space and improving the formation of the solid bone bridge between two adjacent vertebrae by means of a bone substitute internally carried by the prosthesis. To this end, a prosthesis conventionally has several peripheral faces including an upper face and a lower face intended to cooperate with the upper and lower vertebral endplates of the intradiscal space, in other words the lower and upper faces, respectively, of the overlying and underlying vertebrae delimiting the intradiscal space, and these lower and upper faces of the prosthesis are open to an internal space of the prosthesis in which is placed the bone substitute.

Among the prostheses of the prior art, intersomatic prostheses to be introduced in pairs are known, in particular from documents FR 2 946 245 and FR 2 841 124, where two identical prostheses are interposed together between the two vertebrae, by being disposed substantially parallel between the two vertebral bodies on either side of a median plane of the vertebral column (or sagittal plane).

The document FR 2 946 245 discloses an intersomatic prosthesis comprising opposite planar lateral faces having the same height and longitudinally converging to an ogive-shaped anterior end face.

The document FR 2 841 124 discloses a prosthesis comprising opposite curved lateral faces having the same height and longitudinally converging to an ogive-shaped anterior end face.

These prostheses of the prior art are geometrically unsuitable to ensure a good primary stability between the two vertebral bodies, and therefore have the disadvantage of generating risks of pseudarthrosis. In other words, due to a poor geometrical stability of the prosthesis bearings on the upper and lower vertebral endplates of the intradiscal space, these prostheses do not guarantee a good arthrodesis.

The invention offers to overcome this drawback by providing a prosthesis which permanently ensures a strict correlation between the upper and lower bearing faces of the prosthesis and the adjacent vertebral endplates.

Another aim of the invention is to guarantee an almost perfect adjustment of the prosthesis between the two vertebrae, or vertebral bodies, regardless of the lordosis correction that the surgeon wishes to obtain, that is to say, regardless of the lordosis angle imposed by the surgeon.

The invention therefore aims to provide an intersomatic prosthesis which allows to improve the surgical treatment of a patient suffering from a loss of lordosis and/or kyphosis.

To this end, the present invention provides an intersomatic prosthesis for introduction via posterior approach, designed to be introduced in pairs between two vertebral bodies, said prosthesis being composed of a prosthesis body extending along a longitudinal direction of intervertebral introduction, comprising peripheral faces internally delimiting an internal space intended to receive a bone substitute, said peripheral faces comprising:

two opposite lateral faces, respectively an external lateral face and an internal lateral face, said lateral faces being parallel and longitudinally curved in the same direction with a concave internal lateral face and a convex external lateral face, and where the height of the internal lateral face is greater than the height of the external lateral face;

two opposite bearing faces, respectively a lower bearing face and an upper bearing face, where each bearing face has an opening on the internal space;

two opposite end faces, respectively an anterior end face and a posterior end face, said posterior end face having a flat in which are arranged gripping orifices intended to cooperate with a gripping system, and said anterior end face having a general shape of an ogival pyramid with four convex sections, respectively an external lateral section continuously extending the external lateral face, an internal lateral section continuously extending the internal lateral face, a lower section continuously extending the lower bearing face and an upper section continuously extending the upper bearing face;

and wherein:

the lower bearing face has a convex posterior portion of a given radius of curvature, starting from the posterior end face and continuously extended by a convex serrated portion of a given radius of curvature and this serrated portion being extended by the lower section, where the lower section has a radius of curvature smaller than the respective radii of curvature of the posterior and serrated portions of the lower bearing face;

the upper bearing face has a convex posterior portion of a given radius of curvature, starting from the posterior end face and continuously extended by a convex serrated portion of a given radius of curvature and this serrated portion being extended by the upper section, where the upper section has a radius of curvature smaller than the respective radii of curvature of the posterior and serrated portions of the upper bearing face.

Thus, the prosthesis in accordance with the invention has a geometry of these different peripheral faces which ensures a perfect adjustment of the prosthesis between the two vertebrae regardless of the lordosis correction that the surgeon wishes to obtain.

Indeed, this geometry of the prosthesis guarantees a maximization of the contact surface between the lower and upper bearing faces of the prosthesis and the adjacent vertebral endplates, and thus a maximization of the contact surface of the bone substitute (also called bone graft) contained in the internal space of the prosthesis and these vertebral endplates.

Furthermore, the prosthesis shape ensures an increased primary stability, with regard to the prostheses to be introduced in pairs of the prior art, on the vertebral endplates, thus guaranteeing the best results for an arthrodesis of the treated level; bearing in mind that the prosthesis in accordance with the invention is provided to be introduced in pairs between the vertebrae, with a prosthesis in accordance with the invention placed on one side of the sagittal plane of the vertebral column, and another prosthesis in accordance with the invention placed on the other side of the sagittal plane of the vertebral column, and where both prostheses have their opposite internal lateral faces, facing the sagittal plane.

In addition, the ogival pyramid shape with four sections of the anterior end face facilitates the introduction of the prosthesis, to the right or to the left of the sagittal plane, while ensuring a stability between the endplates once set up.

The shape of the prosthesis in accordance with to the invention therefore allows individualizing the positioning of the prosthesis depending on the treated patient, positioning obtained prior to posterior fixation by rotation and sliding of the vertebral bodies on the prosthesis remaining in permanent contact at any point therewith. The present invention therefore provides a prosthesis with a geometrically developed design but whose implementation is simple and which perfectly conforms the shape of the adjacent vertebral endplates without risk of damage of these endplates so that, on the one hand, to ensure a perfect primary stability before osteosynthesis of the treated segment and, on the other hand, to optimally correct a lordosis and/or a kyphosis and thus to improve the surgical treatment.

According to one possibility of the invention, the radius of curvature of the posterior portion of the lower bearing face is smaller than the radius of curvature of the serrated portion of the lower bearing face, and the radius of curvature of the posterior portion of the upper bearing face is smaller than the radius of curvature of the serrated portion of the upper bearing face.

This choice of such an offset between the radii of curvature of the posterior portions and the serrated portions of the upper and lower bearing faces, respectively, is particularly advantageous for the prosthesis to conform the vertebral endplates regardless of the lordosis angle.

According to another possibility of the invention, the serrated portion of the lower bearing face is in tangential connection with both the posterior portion of the lower bearing face and the lower section of the antetior end face, and the serrated portion of the upper bearing face is in tangential connection with both the posterior portion of the upper bearing face and the upper section of the anterior end face.

It is understood by tangential connection between two portions (or a portion and a section) that both convex portions (or the portion and the section) are connected along a junction line and the tangents of both portions coincide on this junction line. Such tangential connections allow avoiding any slope break between the serrated portions and the posterior portions of the respective bearing faces and between the serrated portions and the corresponding sections of the anterior end face. This absence of slope break advantageously participates in improving the suitable geometry for allowing different lordosis angles.

Advantageously, the radius of curvature of the posterior portion of the lower bearing face is equal to the radius of curvature of the posterior portion of the upper bearing face, and the radius of curvature of the serrated portion of the lower bearing face is equal to the radius of curvature of the serrated portion of the upper bearing face.

In this manner, the prosthesis has a symmetry adjusted for a use in pairs of two identical prostheses, on either side of the sagittal plane of the vertebral column.

The invention also concerns the following characteristics, taken independently or in combination:
  the opening of the lower bearing face is arranged along the entire length of the corresponding serrated portion, and the opening of the upper bearing face is arranged along the entire length of the corresponding serrated portion;
  the opening of the lower bearing face represents at least 40% of the lower bearing face, and the opening of the upper bearing face represents at least 40% of the upper bearing face;
  each serrated portion has teeth making an apex angle of 90 degrees and oriented towards the anterior end face along decreasing angles of inclination towards the posterior end face;
  the external lateral face has an oblong-shaped through lumen and extending over at least one third of the total length of the prosthesis body and over at least one third of the total height of the prosthesis body;
  the internal lateral face has at least two through lumens extending over at least half of the total length of the prosthesis body and over at least three quarters of the total height of the prosthesis body.

In a particular embodiment, the prosthesis body has four rounded ridges at the junctions between the lateral faces and the bearing faces, said rounded ridges extending longitudinally from the posterior end face to the anterior end face to extend between the sections and meet at the tip of the anterior end face.

These rounded ridges, which may for example be made in the form of fillets, ensure a smooth introduction of the prosthesis towards the intradiscal space.

According to a particular embodiment, the gripping orifices comprise a bore and a slot extending from the external lateral face to the internal lateral face.

The bore, advantageously placed at the center of the flat, is intended to cooperate with a threaded rod of the gripping system (also called ancillary), while the slot is intended to cooperate with a corresponding shoulder on the gripping system for blocking the rotation of the prosthesis relative to the gripping system.

Advantageously, the anterior end face has in its geometric center a marker made of radio-opaque material.

Still advantageously, the posterior end face has two markers made of radio-opaque material placed in respectively lower and upper opposite corners, of the flat.

Other features and advantages of the present invention will appear upon reading the detailed description below, of a non-restrictive example of implementation, with reference to the appended figures wherein.

Figure 1:
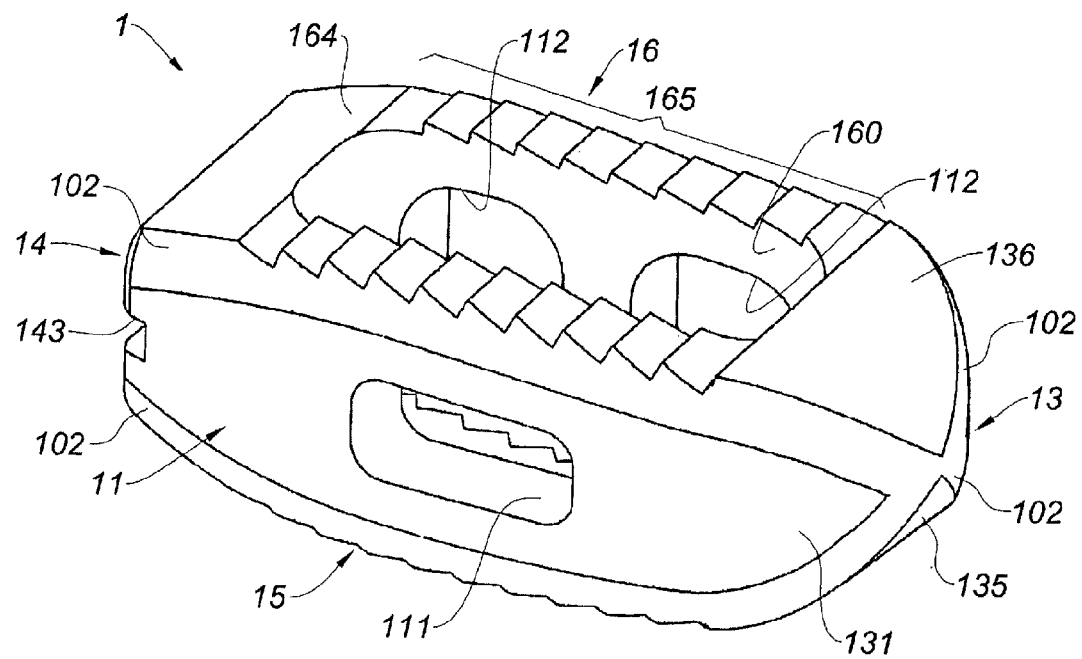
FIG. 1 is a front perspective view of a prosthesis in accordance with the invention, viewed from above and from its external lateral face side.
Figure 2:
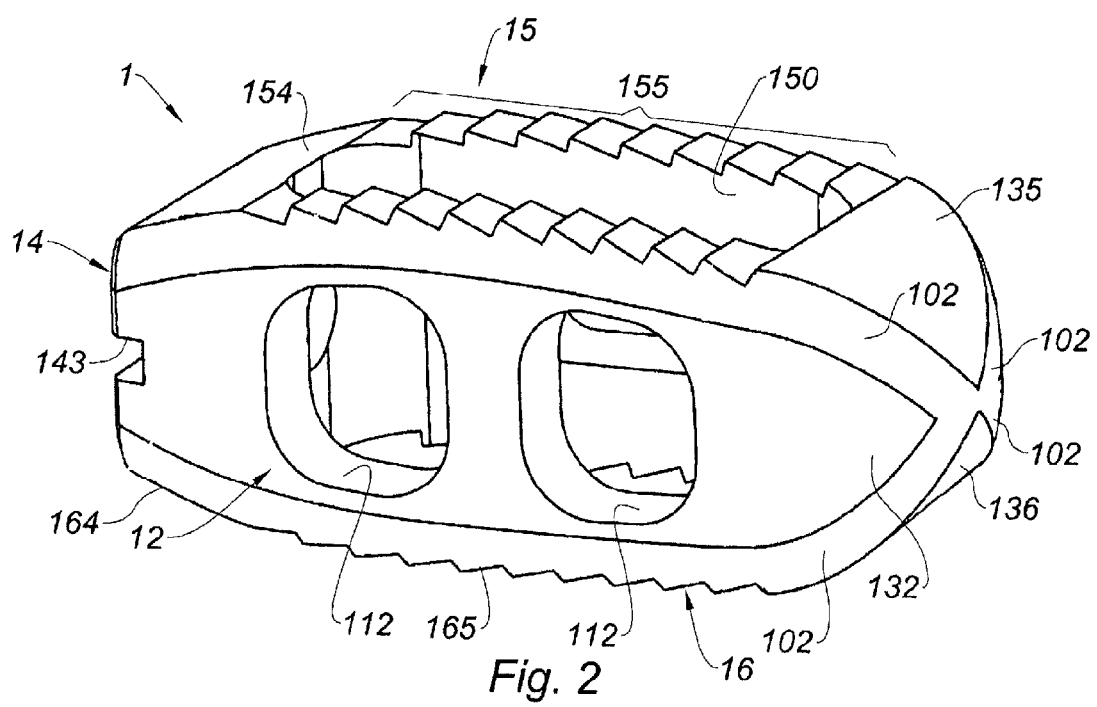
FIG. 2 is a front perspective view of the prosthesis of FIG. 1, viewed from below and from its internal lateral face side.

Referring to the figures, an intersomatic prosthesis 1 in accordance with the invention, is made in one piece in the form of a prosthesis body whose shape substantially fits within that of an elongated parallelepiped. This prosthesis body is made within a bio-implantable or biocompatible material, such as polymer, titanium, stainless steel alloy, mixed metal-polymer alloy, mineral or synthetic material. By way of non-restrictive example, the body is made of polyether-ether-ketone (PEEK), polyether-ketone-ketone (PEKK).

The prosthesis extends along a longitudinal direction which will coincide with its intervertebral introduction direction, in other words the guiding direction of its implantation between the vertebral bodies.

The prosthesis comprises peripheral faces (or walls) 11, 12, 13, 14, 15, 16 internally delimiting an internal space intended to receive a bone substitute, including:

- two opposite lateral faces 11, 12, respectively an external lateral face 11 and an internal lateral face 12, where the internal lateral face 11 is provided to extend in front of the sagittal plane and in front of the internal lateral face 11 of the second prosthesis 1;
- two opposite end faces 13, 14, respectively an anterior end face 13 and a posterior end face 14, the longitudinal direction of the prosthesis 1 extending from the anterior end face 13 towards the posterior end face 14;
- two opposite bearing faces 15, 16, respectively a lower bearing face 15 and an upper bearing face 16, where the lower bearing face 15 abuts against the lower vertebral endplate PI (or the upper vertebral endplate PS, according to the location of the prosthesis 1 vis-à-vis the sagittal plane PG) and the upper bearing face 16 abuts against the upper vertebral endplate PS (or the lower vertebral endplate PI).

The lateral faces 11, 12 are parallel and curved longitudinally in the same direction, that is to say, the internal lateral face 12 is concave (in other words bulging towards the inside of the prosthesis) and the external lateral face 11 is convex (in other words bulging towards the outside of the prosthesis).

In addition, the height H2 of the internal lateral face 12 is greater than the height H1 of the external lateral face 11.

In general, the prosthesis 1 has an average height (average distance between the bearing faces 15, 16) between 5 and 20 millimeters, and particularly between 7 and 16 millimeters. Regardless of the average height of the prosthesis, the height difference between the two lateral faces 11, 12, namely the difference DH=H2−H1, is comprised between 0.7 and 2.2 millimeters, and particularly between 0.8 and 1.2 millimeters, and preferably in the order of 1 millimeter, in order to create a transverse angle equal to at least 5 degrees to adjust to the transverse convexity of the vertebral endplates PI, PS.

Complementarily, the prosthesis 1 has a width (distance between the lateral faces 11, 12) comprised between 8 and 15 millimeters, and particularly comprised between 9.5 millimeters and 11.5 millimeters. Furthermore, the prosthesis 1 has a length (distance between the end faces 13, 14) comprised between 15 and 40 millimeters, particularly between 22 and 34 millimeters.

The external lateral face 11 has a through lumen 111 opening into the internal space intended to receive the bone substitute. This lumen 111 is oblong and extends longitudinally over at least one third of the total length of the prosthesis body and vertically (between both bearing faces 15, 16) on at least one third of the total height of the prosthetic body. This lumen 111 has an advantageous effect of providing the external lateral face 11 with a dynamic elasticity, particularly in order to facilitate the introduction and the support of the prosthesis 1 between the vertebral endplates PI, PS.

The internal lateral face 12 has at least two through lumens 112, opening into the internal space intended to receive the bone substitute. These lumens 112 extend longitudinally over at least half of the total length of the prosthesis body and vertically over at least three quarters of the total height of the prosthesis body. These lumens 112 are preferably higher than the lumen 111. These lumens 112 enable the contact between the bone substitute located inside the prosthesis 1 in the internal space and the bone substitute located outside the prosthesis 1. These lumens 112 also have the advantageous effect of providing the internal lateral face 12 with a dynamic elasticity.

The posterior end face 14 having a flat 141 in which are arranged gripping orifices 142, 143 intended to cooperate with a gripping system (not illustrated). More specifically, these gripping orifices 142, 143 comprise:

- a bore 142 arranged at the center of the flat 141; and
- a slot 143 extending over the entire width of the flat 141, from the external lateral face 11 to the internal lateral face 12.

The bore 142 which opens into the internal space is intended to cooperate with a threaded rod of the gripping system and the slot 143 is provided to cooperate with a corresponding shoulder on the gripping system in order to block the rotation of the prosthesis 1 with respect to the gripping system.

The anterior end face 13 having a general shape of an ogival pyramid with four convex sections, respectively:

- an external lateral section 131 continuously extending the external lateral face 11;
- an internal lateral section 132 continuously extending the internal lateral face 12;
- a lower section 135 continuously extending the lower bearing face 15; and
- an upper section 136 continuously extending the upper bearing face 16.

The bearing faces 15, 16 each having an opening 150, 160 opening onto the internal space of the prosthesis 1, to subsequently enable contact between the vertebral endplates PI, PS and the bone substitute located inside the prosthesis 1 in the internal space. The opening 150 of the lower bearing face 15 can cover at least 40% of the lower bearing face 15. The opening 160 of the upper bearing face 16 can cover at least 40% of the upper bearing face 16.

The lower bearing face 15 has two longitudinally successive portions, namely:
- a posterior portion 154 starting from the posterior end face 14; and
- a serrated portion 155 which continuously extends, without slope break, the posterior portion 154 to the lower section 135 of the anterior end face 13.

The posterior portion 154 is convex, in other words bulging towards the outside of the prosthesis, and has a given radius of curvature R1.

The opening 150 of the lower bearing face 15 is arranged over the entire length of the serrated portion 155, such that this serrated portion 155 has the shape of two internal and external serrated edges, separated from each other by the opening 150, and located respectively on the side of the internal and external lateral faces 12, 11. These internal and external serrated edges have a vertical offset due to the difference in height between the lateral faces 11, 12.

The serrated portion 155 is convex, in other words bulging towards the outside of the prosthesis, and has a given radius of curvature R2. This radius of curvature R2 is greater than the radius of curvature R1 of the posterior portion 154.

The radius of curvature R1 is comprised between 20 and 40 millimeters, particularly between 23 and 35 millimeters. The radius of curvature R2 is comprised between 80 and 110 millimeters, and particularly between 90 and 100 millimeters. The larger (or longer) the prosthesis 1, the greater the radii of curvature R1 and R2.

In addition, this serrated portion 155 is in tangential connection with both the posterior portion 154 and the lower section 135 of the anterior end face 13, which guarantees continuity without slope break of the top or upper part of the prosthesis, with a continuously variable convexity.

The lower section 135 is convex, in other words bulging towards the outside of the prosthesis, and has a given radius of curvature R3 which is smaller than the radii of curvature R1 and R2.

The radius of curvature R3 is comprised between 3 and 6 millimeters, particularly between 4.5 and 5.5 millimeters. The larger (or longer) the prosthesis 1 the greater the radius of curvature R3.

The upper bearing face 16 has two longitudinally successive portions, namely:
- a posterior portion 164 starting from the posterior end face 14; and
- a serrated portion 165 which continuously extends, without slope break, the posterior portion 164 to the upper section 136 of the anterior end face 13.

The posterior portion 164 is convex, in other words bulging towards the outside of the prosthesis, and has a radius of curvature R1 equal to that of the posterior portion 154 of the lower bearing face 15.

The opening 160 of the upper bearing face 16 is arranged over the entire length of the serrated portion 165, so that this serrated portion 165 has the shape of two internal and external serrated edges, separately from each other by the opening 160, and located respectively on the side of the internal and external lateral faces 12, 11. These internal and external serrated edges have a vertical offset due to the difference in height between the lateral faces 11, 12.

The serrated portion 165 is convex, in other words bulging towards the outside of the prosthesis, and has a radius of curvature R2 equivalent to that of the serrated portion 155 of the lower bearing face 15. This radius of curvature R2 is thus greater than the radius of curvature R1 of the posterior portion 164.

In addition, this serrated portion 165 is in tangential connection with both the posterior portion 164 and the upper section 136 of the anterior end face 13, which guarantees continuity without slope break of the bottom or lower part of the prosthesis, with a continuously variable convexity.

The upper section 136 is convex, in other words bulging towards the outside of the prosthesis, and has a radius of curvature R3 equivalent to that of the lower section 135, so which is lower than the radii of curvature R1 and R2.

Thus, the bearing faces 15, 16 each have a convex profile with continuously variable convexity in the longitudinal direction, this convexity being directed towards the outside of the prosthesis body and extending from the posterior end face 14 to the anterior end face 13 and joining without discontinuity or slope break to the corresponding sections 135, 136 of the anterior end face 13.

Due to the specific geometry of the bearing faces 15, 16, and particularly due to the continuous variation and without slope break of the convexity of the bearing faces 15, 16, these bearing faces 15, 16 can almost ideally interleave between the surfaces of the vertebral endplates PI, PS, achieving a perfect correlation of both surfaces like a mold on a molded piece.

Figure 7:
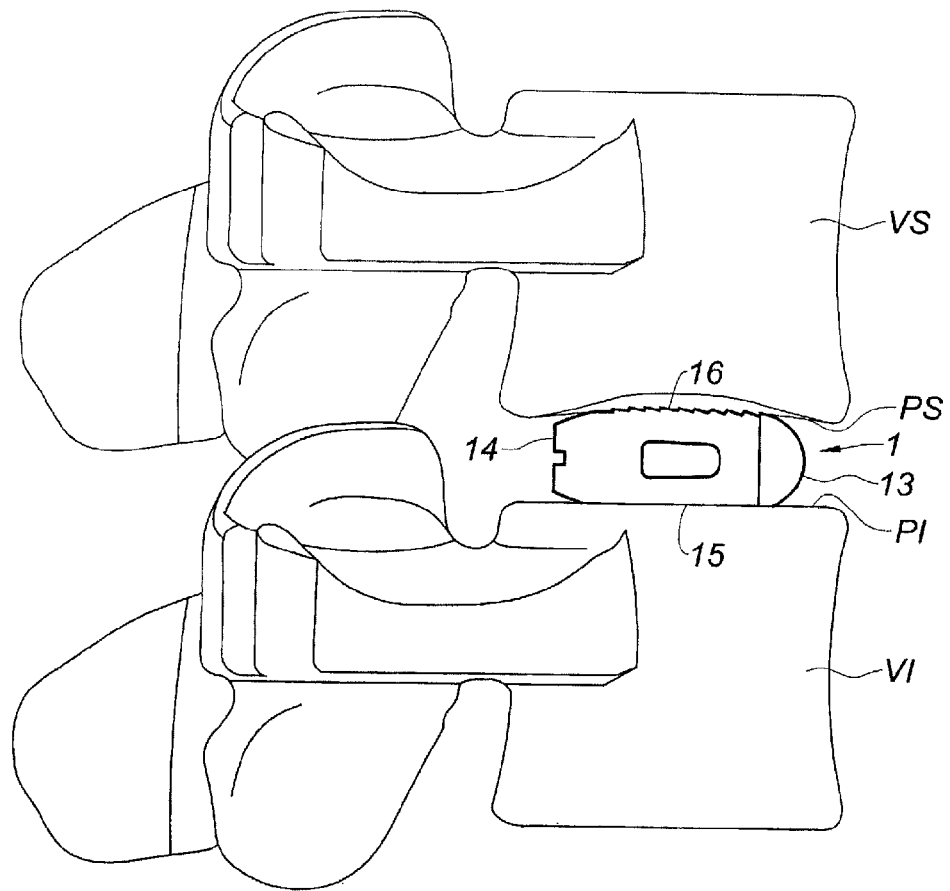
FIG. 7 is a side view of a prosthesis in accordance with FIGS. 1 and 2, in place between lower and upper endplates of an intradiscal space.
Figure 8:
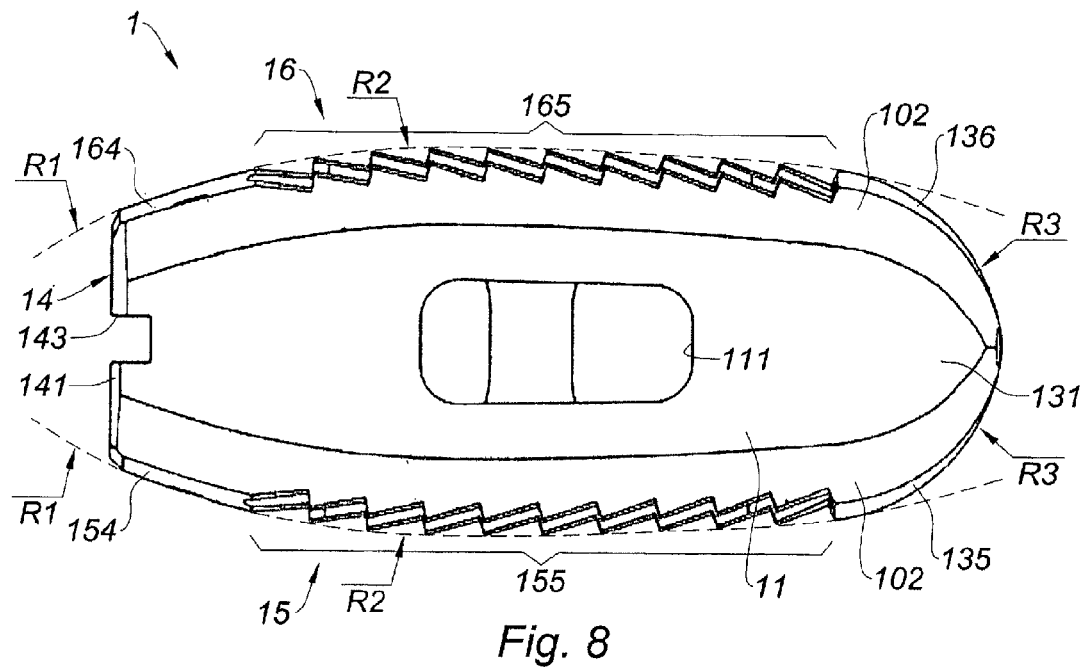
FIG. 8 is a side view of the prosthesis of FIG. 1, viewed from its external lateral face side.

The height difference H1, H21 between the lateral faces 11, 12 allows the prosthesis 1 to have both a longitudinal convexity (lengthwise, from the posterior end face 14 to the anterior end face 13) and a lateral convexity (widthwise between the internal lateral face 12 and the external lateral face 11, due to the difference of aforementioned height). As visible in FIGS. 5 and 7, this double convexity ensures keeping the continuous contact over the entire periphery of the prosthesis 1 with the vertebral endplates PI, PS, regardless of the lordosis angle.

Figure 9A:
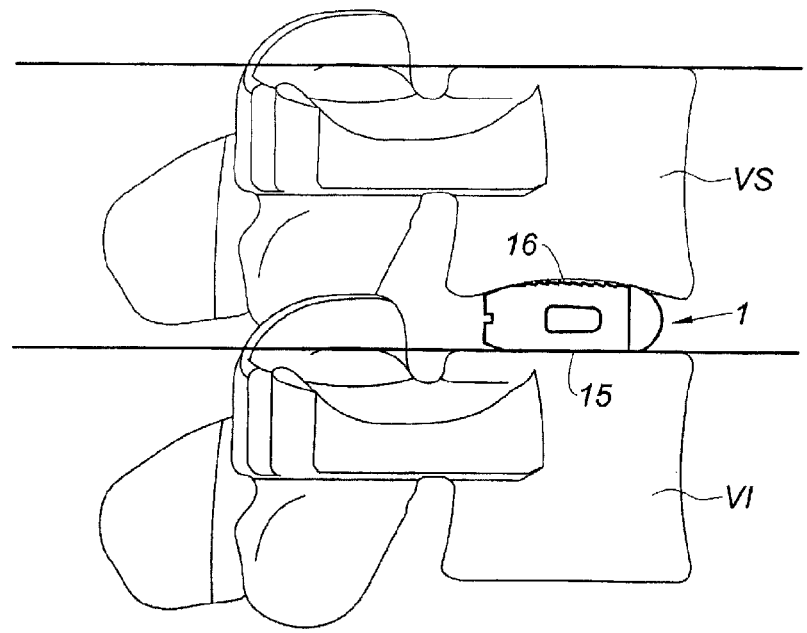
FIGS. 9a to 9c are views identical to that of FIG. 7, with several distinct lordosis angles, namely a zero lordosis angle (FIG. 9a), a 6 degrees lordosis angle (FIG. 9b) and a 12 degrees lordosis angle (FIG. 9c)
Figure 9B:
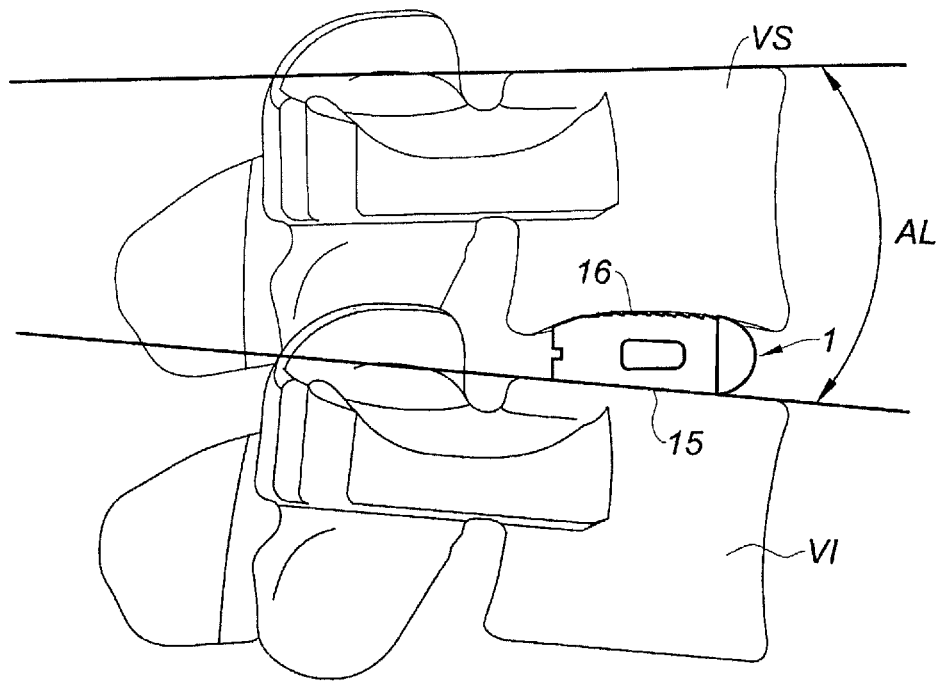
Figure 9C:
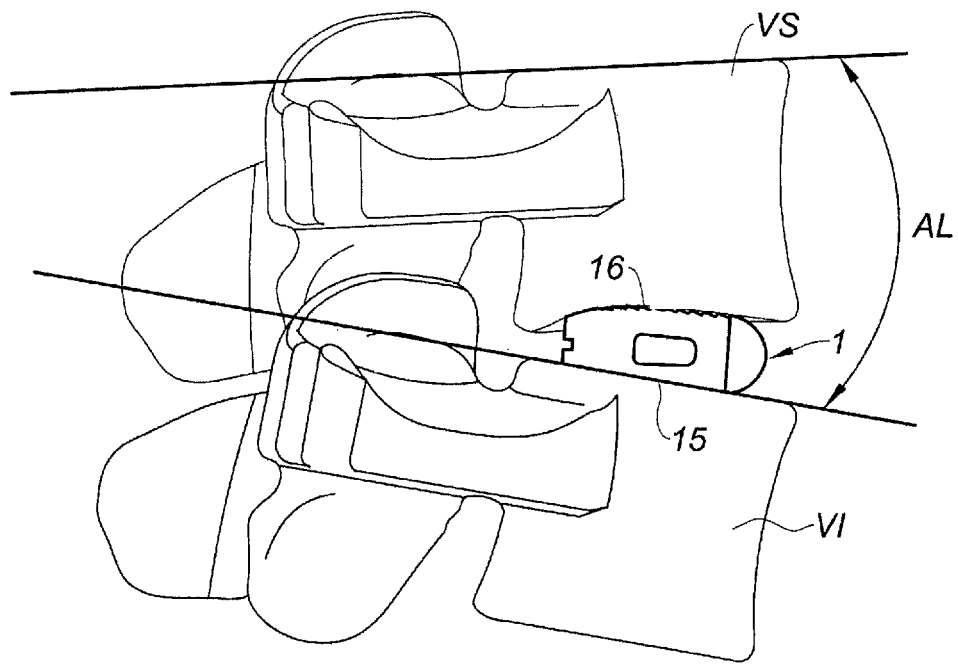

As schematically illustrated in FIGS. 9a to 9c, the bearing faces 15, 16 of the prosthesis 1 remain, due to this continuously variable convexity and without slope break, in permanent correlation with the surfaces of the vertebral endplates PI, PS, regardless of the lordosis angle AL provided to obtain sagittal balance. Thus, this continuously variable convexity without slope break of the bearing faces 15, 16 allow the choice among multiple possible lordosis angles, this free choice having the advantageous consequence to obtain a sagittal balance perfectly individualized and adapted to the treated patient, which balance results in a better load distribution and a decrease in degeneration of the adjacent segments.

Thus, the advantage of the prosthesis 1 is to allow an individualized lordosis, that is to say, the surgeon can decide, during the intraoperatively phase, of the lordosis degree he wants to obtain; the lordosis being conventionally obtained by subsequently compressing with a contracting clamp on screws. This choice of lordosis angle is made depending on the physiology of the patient and is made possible thanks to the shape particularly examined of the bearing faces 15, 16 which are formed from multiple radii of curvatures carefully selected and distributed, and thanks to the shape of the lateral faces 11, 12, so that the bearing faces 15, 16 remain in contact with the vertebral endplates PI, PS regardless of the lordosis angle AL selected by the surgeon.

In the three cases illustrated in FIGS. 9a to 9c, the bearing faces 15,16 are in contact with the vertebral endplates PI, PS, which ensures an excellent primary stability (that is to say before bone fusion with bone substitute). In addition, the bone substitute contained in the prosthesis 1 also remains in contact and is compressed between the vertebral endplates PI, PS, which guarantees obtaining a rapid fusion.

Each serrated portion 155, 165 has teeth making an apex angle of 90 degrees and oriented towards the anterior end face 13 along decreasing angles of inclination towards the posterior end face 14. These teeth have a maximum height of one even two millimeters. These teeth are oriented towards the anterior end face 13, which orientation vis-à-vis the longitudinal direction varying gradually from 5 degrees to 20 degrees due to the convexity of the serrated portion 155 or 165. Each serrated portion 155, 165 thus offers carefully both a non-aggressive surface for the vertebral endplates PI, PS and a good grip in these vertebral endplates PI, PS, which grip guaranteeing an excellent primary stability thus avoiding the risks of mobility, collapse and pseudarthrosis.

The prosthesis body also has four rounded ridges 102 at the junctions between the lateral faces 11, 12 and the bearing faces 15, 16, therefore with a first rounded ridge 102 between the internal lateral face 12 and the lower bearing face 15, a second rounded ridge 102 between the internal lateral face 12 and the upper bearing face 16, a third rounded ridge 102 between the external lateral face 11 and the lower bearing face 15, and finally a fourth rounded ridge 102 between the external lateral face 11 and the upper bearing face 16.

These rounded ridges 102, which are particularly in the form of fillets, extending longitudinally from the posterior end face 14 to the anterior end face 13 to extend also between the sections 131, 132, 135, 136 and meet at the tip of the anterior end face 13. Thus, the first rounded ridge 102 also extends between the internal lateral section 132 and the lower section 135, the second rounded ridge 102 also extends between the internal lateral section 132 and the upper section 136, the third rounded ridge 102 also extends between the external lateral section 131 and the lower section 135, and finally the fourth rounded ridge also extends between the external lateral section 131 and the upper section 136.

Thus, these rounded ridges 102 extend without slope discontinuity of the flat 141 from the posterior end face 14 to the tip (or top) of the anterior end face 13, the junction of the four rounded ridges 102 at the top of the anterior end face 13 allowing a safe and totally atraumatic impaction of the prosthesis 1 when introduced between the vertebral endplates PI, PS, these rounded ridges 102 following the curvature of the lateral faces 11, 12 thus preserving the neurological structures located on the approach.

Figure 11:
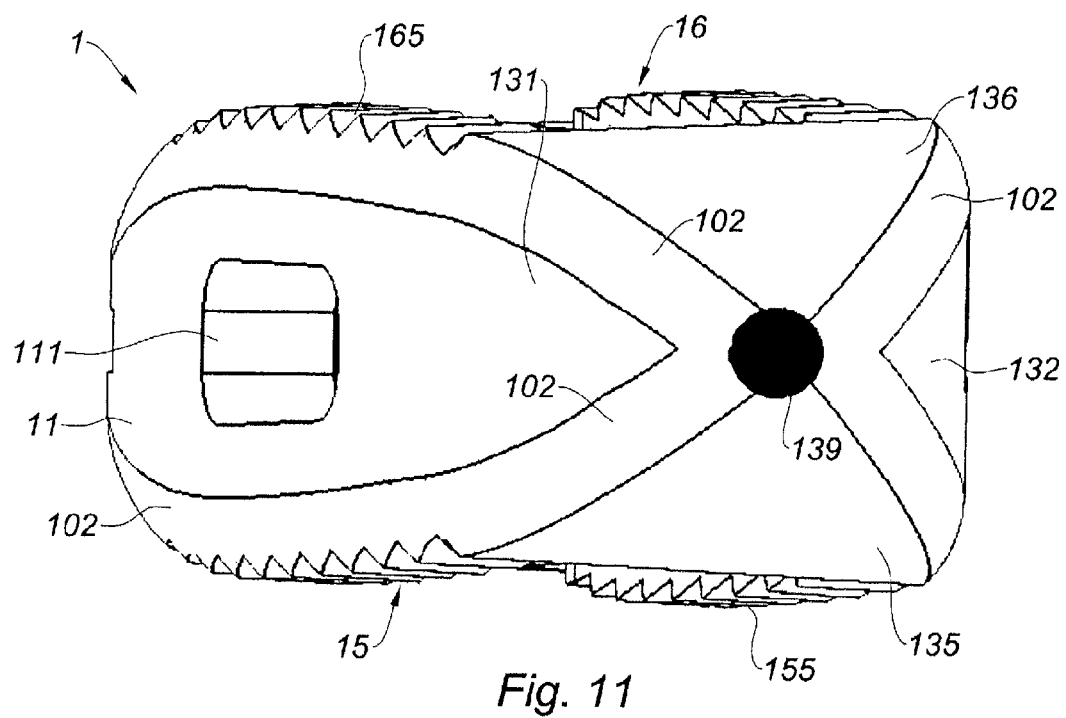
FIG. 11 is a front perspective view of the prosthesis of FIG. 1, with a central marker on its anterior end face.

As visible in FIG. 11, the anterior end face 13 has at its geometric center (in other words at the top where the four rounded ridges meet) a marker 139 made of radio-opaque material. This marker 139 is for example of a spherical shape, and particularly with a diameter in the order of one millimeter.

Figure 10:
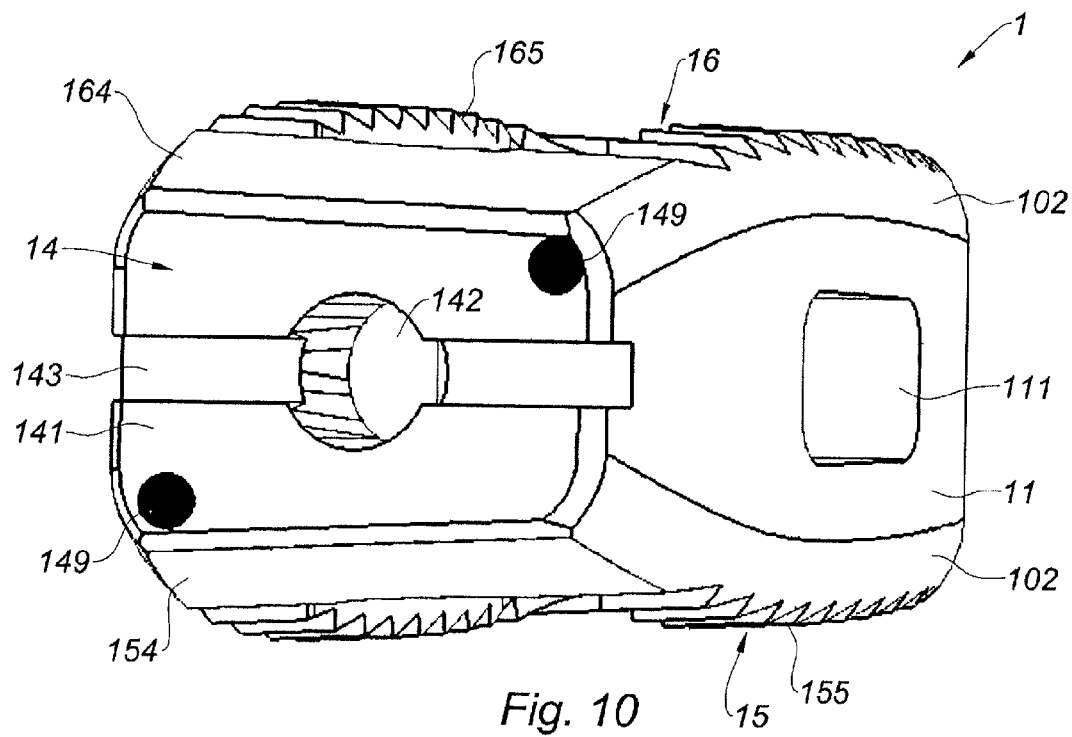
FIG. 10 is a rear perspective view of the prosthesis of FIG. 1, with two diagonal markers on its posterior end face.

As visible in FIG. 10, the posterior end face 14 has two markers 149 made of radio-opaque material placed in respectively lower and upper opposite corners of the flat 141, for example with a first marker in the upper and external corner of the flat 141 and a second marker in the lower and internal corner of the flat 141.

These markers 149 are thus opposite along a diagonal of the flat 141, and are for example identical to the marker 139 positioned on the top of the anterior end face 13.

This disposition of the markers 139, 149 allows that, during a radiographic shot in the frontal plane, the three markers 139, 149 are aligned along a 45 degrees inclined direction from outside to inside.

Figure 3:
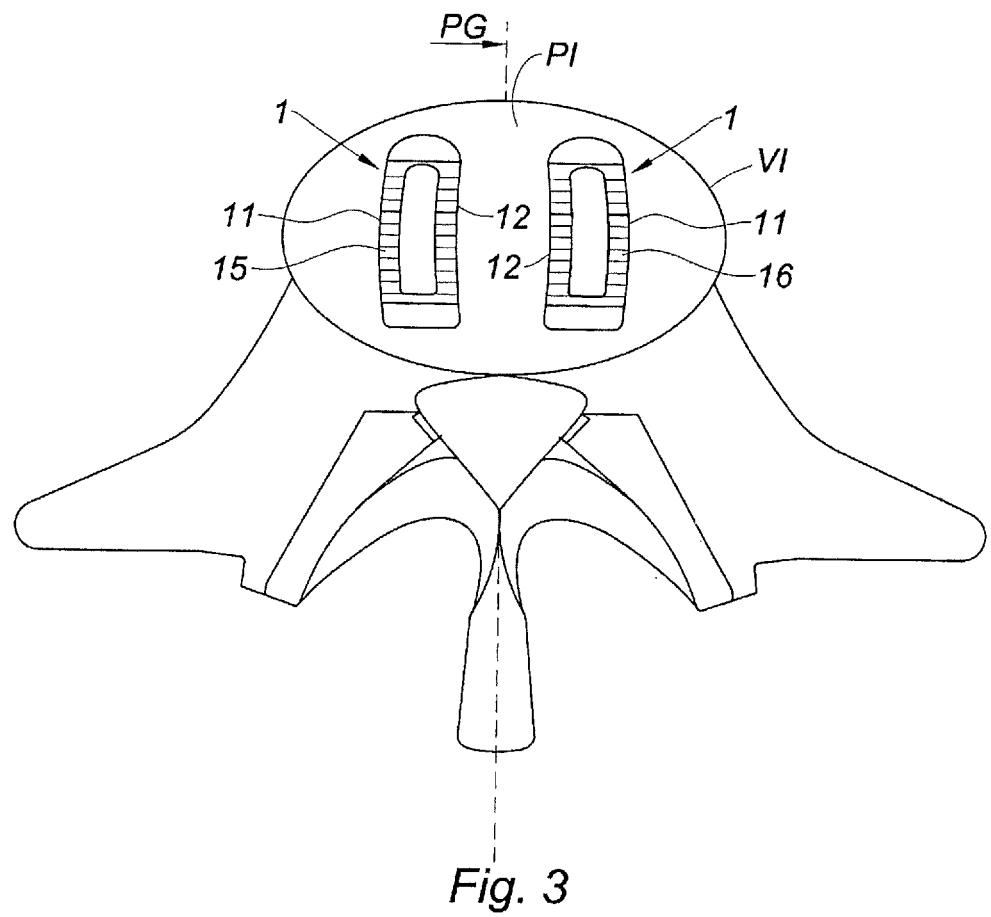
FIG. 3 is a schematic top view of two prostheses in accordance with FIGS. 1 and 2, in place on a lower endplate of an intradiscal space, formed of the upper face of an underlying vertebra.
Figure 4:
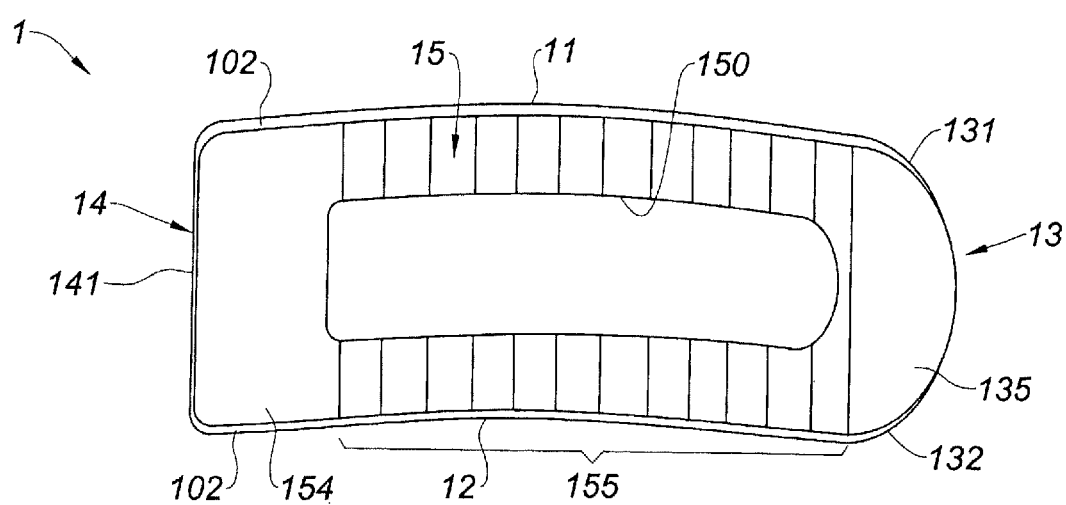
FIG. 4 is a bottom view of the prosthesis of FIG. 1.
Figure 5:
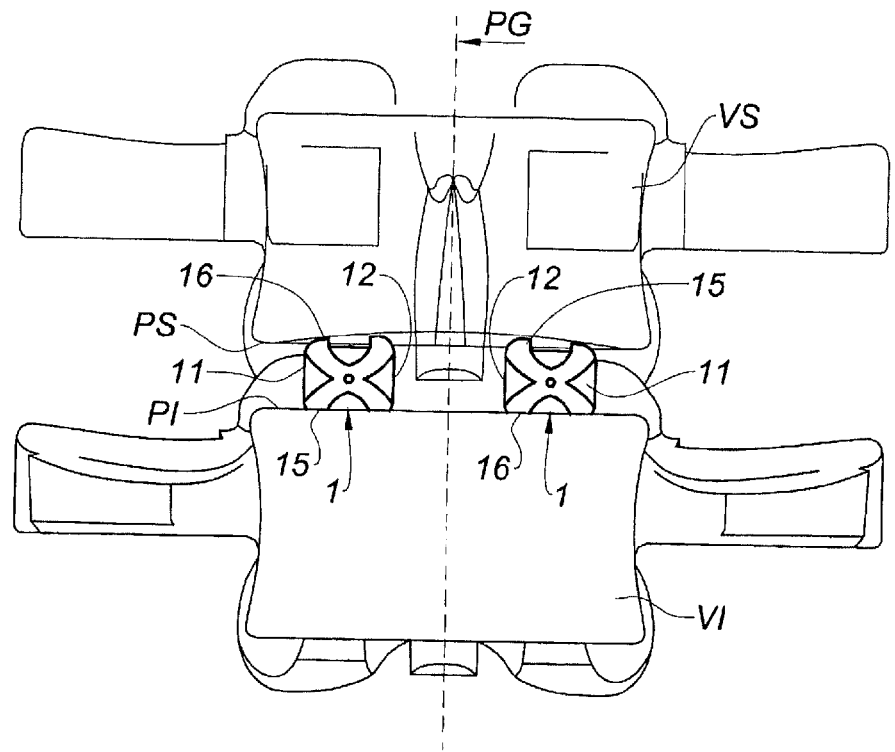
FIG. 5 is a schematic frontal (or front) view of two prostheses in accordance with FIGS. 1 and 2, in place between the upper and lower endplates of an intradiscal space, formed respectively of upper and lower faces of overlying and underlying vertebrae.
Figure 6:
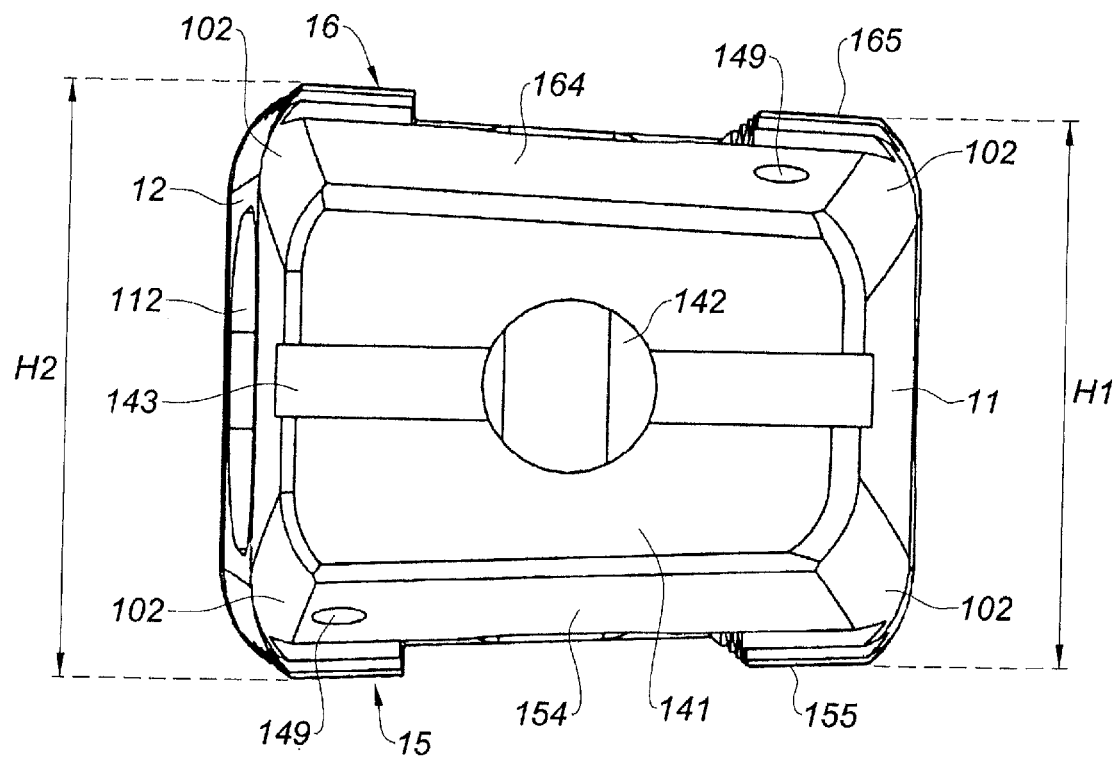
FIG. 6 is a back (or rear) view of the prosthesis of FIG. 1.

As visible in FIGS. 3 and 5, such a prosthesis 1 is implanted in duplicate. In other words, a first prosthesis 1 is introduced between the vertebral endplates PI, PS to the right of the sagittal plane PG, and a second prosthesis 1 is introduced between the vertebral endplates PI, PS to the left of the sagittal plane PG. Once placed, the internal lateral faces 12 of the two prostheses are facing each other and both prostheses extend substantially parallel on either side of the sagittal plane PG.

The two prostheses 1 are identical, and differ in that one is turned by 180° relative to the other so that the first prosthesis 1 has its upper bearing face 16 against the upper vertebral endplate PS and its lower bearing face 15 against the lower vertebral endplate PI, while the second prosthesis 1 has its upper bearing face 16 against the lower vertebral endplate PI and its lower bearing face 15 against the upper vertebral endplate PS.

Each prosthesis 1 is implantable by endoscopy or open surgery. If necessary, the prosthesis can be removed. The prosthesis 1 is intended for the treatment of individuals suffering from degenerative disc disease at the thoracic or lumbar vertebrae, for insertion between the vertebral bodies of these thoracic or lumbar vertebrae.

This prosthesis 1 is particularly advantageous because it allows making its bearing faces 15, 16 cooperate with the vertebral endplates PI, PS with the maximum contact surface regardless of the lordosis correction angle AL that the surgeon wishes to give to the operated segment.

The angular adjustment of the support surface area of the prosthesis 1 of the present invention thus generates an unexpected and surprising effect of primary stability of the prosthesis 1 due to a continuous contact between the vertebral endplates PI, PS and the bearing faces 15, 16 of the prosthesis 1, an effect which is consecutively accompanied by a correction of optimal lordosis and/or kyphosis because it is individualized.

Such a prosthesis 1 thus advantageously differs from the known prostheses which are prostheses with fixed lordosis angle, with which the surgeon must select a prosthesis providing a given lordosis angle and which cannot adjust the lordosis correction once the prosthesis is inserted between the vertebral bodies.

With the invention, the angular adjustment of the lordosis angle AL can be made after the pair of prostheses 1 has been positioned between vertebral bodies. This adjustment results in ensuring a better transmission of loads thanks to the continuous contact with the vertebral endplates PI, PS and thus guarantees to the patient a better sagittal balance.

An advantageous corollary of this result is to significantly reduce risks of degenerative disc disease on the adjacent levels, known as the transitional junction syndrome or discopathy of the adjacent segment. Indeed, it is perfectly established that a balanced reconstruction of the spine minimizes the efforts and actions of the back muscles but also of the legs because the patient does not work his body to "straighten the spine" in the optimal position. The present invention allows the surgeon to perform a reconstruction and to obtain a lordosis correction promoting optimal sagittal balance, thus reducing the risks of re-operation consecutive to a degeneration of the adjacent segments.

The invention claimed is:

1. An intersomatic prosthesis for introduction via posterior approach, designed to be introduced in pairs between two vertebral bodies on either side of a sagittal plane of a vertebral column, said prosthesis being composed of a prosthesis body extending along a longitudinal direction of intervertebral introduction, comprising peripheral faces internally delimiting an internal space intended to receive a bone substitute, said peripheral faces comprising:

a convex external lateral face and a concave internal lateral face opposite the convex external lateral face, said lateral faces being parallel and longitudinally curved in the same direction, wherein a height of the concave internal lateral face is greater than a height of the convex external lateral face;

a lower bearing face and an upper bearing face opposite the lower bearing face, wherein each bearing face has an opening on the internal space;

an anterior end face and a posterior end face opposite the anterior end face, said posterior end face having a flat in which are arranged gripping orifices intended to cooperate with a gripping system, and said anterior end face having a general shape of ogival pyramid with four convex sections, respectively an external lateral section continuously extending the convex external lateral face, an internal lateral section continuously extending the concave internal lateral face, a lower section continuously extending the lower bearing face and an upper section continuously extending the upper bearing face; and wherein:

the lower bearing face comprises a convex posterior portion having a radius of curvature between 20 and 40 millimeters and starting from the posterior end face and continuously extended by a convex serrated portion having a radius of curvature between 80 and 110 millimeters, the convex serrated portion being extended by the lower section, wherein the lower section has a radius of curvature between 3 and 6 millimeters, the upper bearing face comprises a convex posterior portion having a radius of curvature between 20 and 40 millimeters and starting from the posterior end face and continuously extended by a convex serrated portion having a radius of curvature of between 80 and 110 millimeters, the convex serrated portion being extended by the upper section, wherein the upper section has a radius of curvature of between 3 and 6 millimeters, and the prosthesis body has four rounded ridges at the junctions between the lateral faces and the bearing faces, the four rounded ridges extending longitudinally from the posterior end face to the anterior end face to extend between the convex sections of the anterior end face, and the four rounded ridges meet at a tip of the anterior end face, the four rounded ridges comprising:

a first rounded ridge extending between the concave internal lateral face and the lower bearing face, and also extending between the internal lateral section and the lower section of the anterior end face, a second rounded ridge extending between the concave internal lateral face and the upper bearing face, and also extending between the internal lateral section and the upper section of the anterior end face, a third rounded ridge extending between the convex external lateral face and the lower bearing face, and also extending between the external lateral section and the lower section of the anterior end face, and a fourth rounded ridge extending between the convex external lateral face and the upper bearing face, and also extending between the external lateral section and the upper section of the anterior end face.

2. The prosthesis according to claim 1, wherein the convex serrated portion of the lower bearing face is in tangential connection with both the convex posterior portion of the lower bearing face and the lower section of the anterior end face, and the convex serrated portion of the upper bearing face is in tangential connection with both the convex posterior portion of the upper bearing face and the upper section of the anterior end face.

3. The prosthesis according to claim 1, wherein the radius of curvature of the convex posterior portion of the lower bearing face is equal to the radius of curvature of the convex posterior portion of the upper bearing face, and the radius of curvature of the convex serrated portion of the lower bearing face is equal to the radius of curvature of the convex serrated portion of the upper bearing face.

4. The prosthesis according to claim 1, wherein the opening of the lower bearing face is arranged over the entire length of the corresponding convex serrated portion, and the opening of the upper bearing face is arranged over the entire length of the corresponding convex serrated portion.

5. The prosthesis according to claim 1, wherein the opening of the lower bearing face represents at least 40% of the lower bearing face, and the opening of the upper bearing face represents at least 40% of the upper bearing face.

6. The prosthesis according to claim 1, wherein each convex serrated portion has teeth making an apex angle of 90 degrees and oriented towards the anterior end face along decreasing angles of inclination towards the posterior end face.

7. The prosthesis according to claim 1, wherein the convex external lateral face has an oblong-shaped through lumen and extending over at least one third of the total length of the prosthesis body and over at least one third of the total height of the prosthesis body.

8. The prosthesis according to claim 1, wherein the concave internal lateral face has at least two through lumens extending over at least the half of the total length of the prosthesis body and over at least the three quarters of the total height of the prosthesis body.

9. The prosthesis according to claim 1, wherein the gripping orifices comprise a bore and a slot extending from the external lateral face to the internal lateral face.

10. The prosthesis according to claim 1, wherein the anterior end face has in its geometric center a marker made of radio-opaque material.

11. The prosthesis according to claim 1, wherein the posterior end face comprises two markers made of radio-opaque material placed in respectively lower and upper opposite corners of the flat.

* * * * *